(12) United States Patent
Onishi et al.

(10) Patent No.: US 8,707,972 B2
(45) Date of Patent: Apr. 29, 2014

(54) ENDOSCOPE PROCESSING APPARATUS AND ENDOSCOPE PROCESSING METHOD

(75) Inventors: Hideto Onishi, Hachioji (JP); Daisaku Negoro, Saitama (JP); Yoko Negoro, legal representative, Saitama (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/359,573

(22) Filed: Jan. 27, 2012

(65) Prior Publication Data

US 2012/0211033 A1 Aug. 23, 2012

Related U.S. Application Data

(63) Continuation of application No. PCT/JP2011/069807, filed on Aug. 31, 2011.

(30) Foreign Application Priority Data

Sep. 14, 2010 (JP) .................................. 2010-205895

(51) Int. Cl.
*B08B 3/00* (2006.01)
(52) U.S. Cl.
USPC .................................................. 134/102.1
(58) Field of Classification Search
None
See application file for complete search history.

(56) References Cited

U.S. PATENT DOCUMENTS

2010/0022839 A1    1/2010   Onishi et al.

FOREIGN PATENT DOCUMENTS

| EP | 2 147 656 A1 | 1/2010 |
|---|---|---|
| EP | 2 305 098 A1 | 4/2011 |
| JP | 58-156384 | 9/1983 |
| JP | 06-133929 | 5/1994 |
| JP | 2006-068095 | 3/2006 |
| JP | 2010-022771 | 2/2010 |
| WO | WO 2010/010787 A1 | 1/2010 |

*Primary Examiner* — Jason Ko
(74) *Attorney, Agent, or Firm* — Scully, Scott, Murphy & Presser, P.C.

(57) ABSTRACT

An endoscope processing apparatus of the invention includes: a cleaning tank which can house an endoscope; a liquid drainage port, a liquid inlet port and a discharge port which are opening portions provided to the cleaning tank; a first-liquid introducing section which introduces a first liquid into a multipurpose conduit; a second-liquid introducing section which introduces a second liquid into the multipurpose conduit; a gas-liquid mixing section which mixes a liquid in the multipurpose conduit with gas, to deliver the mixed fluid to the discharge port; a liquid-feeding section which delivers a liquid in the multipurpose conduit to the gas-liquid mixing section; and an opening/closing section which opens and closes a connection between the multipurpose conduit and the gas-liquid mixing section; and a compressor which delivers the gas to the gas-liquid mixing section.

2 Claims, 11 Drawing Sheets

ENDOSCOPE PROCESSING APPARATUS AND ENDOSCOPE PROCESSING METHOD

CROSS REFERENCE TO RELATED APPLICATION

This application is a continuation application of PCT/JP2011/069807 filed on Aug. 31, 2011 and claims benefit of Japanese Application No. 2010-205895 filed in Japan on Sep. 14, 2010, the entire contents of which are incorporated herein by this reference.

BACKGROUND OF THE INVENTION

1. Field of the Invention

The present invention relates to an endoscope processing apparatus and an endoscope processing method that process an endoscope using a mixed liquid obtained by mixing a plurality of liquids.

2. Description of the Related Art

Endoscopes used in medical fields are subjected to a cleaning processing and a disinfection processing after use by using a medicinal solution. The endoscope processing apparatus which automatically performs at least one of a cleaning processing and a disinfection processing of an endoscope is disclosed in Japanese Patent Application Laid-Open Publication No. 2006-68095, for example. The endoscope processing apparatus disclosed in the Japanese Patent Application Laid-Open Publication No. 2006-68095 is an apparatus which performs a cleaning processing of an endoscope using ozone water obtained by dissolving ozone in water, as a medicinal solution, and the ozone water is temporarily stored in a tank.

In addition, there are known endoscope apparatuses configured to generate a medicinal solution for processing an endoscope by mixing a plurality of liquids at a predetermined ratio. The endoscope apparatuses thus configured are provided with a mixing tank for mixing a plurality of liquids, and a liquid level sensor used for pouring a plurality of liquids into the mixing tank by predetermined amounts.

Furthermore, as disclosed in Japanese Patent Application Laid-Open Publication No. S58-156384, a method of flowing two-phase gas-liquid flow (TPF), which is obtained by mixing gas and liquid at a predetermined ratio, into a conduit is known as a method of effectively cleaning a conduit provided to an endoscope.

SUMMARY OF THE INVENTION

An endoscope processing apparatus according to the present invention includes: a cleaning tank configured to be able to house at least one of an endoscope and endoscope accessories; a liquid drainage port which is an opening portion provided to the cleaning tank; a liquid inlet port which is an opening portion provided to the cleaning tank; a discharge port which is an opening portion provided to the cleaning tank; a multipurpose conduit connected to the liquid inlet port; a first-liquid introducing section connected to the multipurpose conduit and configured to introduce a first liquid into the multipurpose conduit; a second-liquid introducing section connected to the multipurpose conduit and configured to introduce a second liquid into the multipurpose conduit; a gas-liquid mixing section connected to the multipurpose conduit and the discharge port, and configured to mix a liquid in the multipurpose conduit and gas, to deliver the mixed fluid to the discharge port; a liquid-feeding section provided between the multipurpose conduit and the gas-liquid mixing section, and configured to deliver a liquid in the multipurpose conduit to the gas-liquid mixing section; an opening/closing section provided between the multipurpose conduit and the gas-liquid mixing section, and configured to open and close a connection between the multipurpose conduit and the gas-liquid mixing section; and a compressor connected to the gas-liquid mixing section, and configured to deliver the gas to the gas-liquid mixing section.

In addition, an endoscope processing method according to the present invention is a method of processing at least one of an endoscope and endoscope accessories by using the endoscope processing apparatus, the method includes: a first-liquid introducing process in which a first liquid is filled in the multipurpose conduit by using the first-liquid introducing section; a second-liquid introducing process in which a predetermined amount of second liquid is introduced into the multipurpose conduit by using the second-liquid introducing section; a stirring process in which a liquid in the multipurpose conduit is delivered to the gas-liquid mixing section by operating the liquid-feeding section with an opening/closing section being opened; and a two-phase gas-liquid flow cleaning process in which a liquid in the multipurpose conduit is delivered to the gas-liquid mixing section by operating the liquid-feeding section and the liquid-feeding section and the gas is delivered to the gas-liquid mixing section by operating the compressor, with the opening/closing section being closed.

DETAILED DESCRIPTION OF THE PREFERRED EMBODIMENTS

Figure 1:
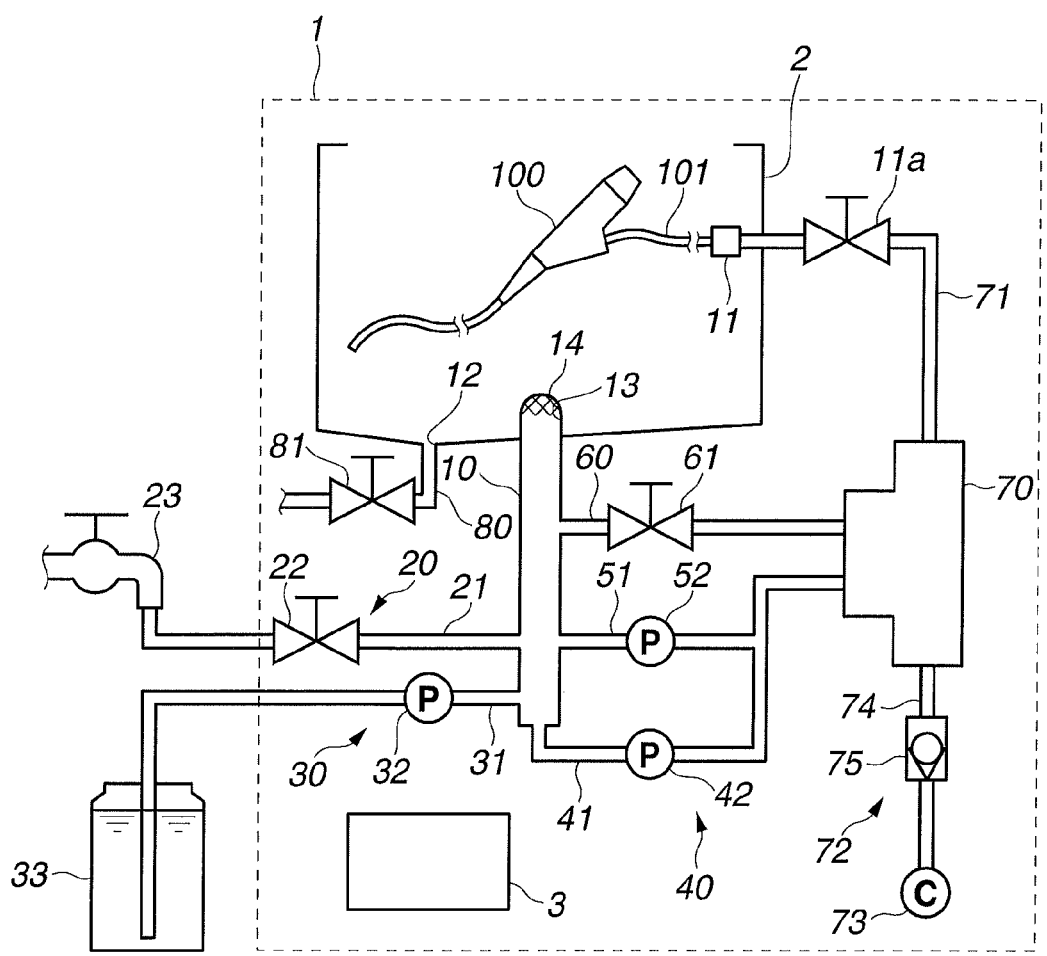
FIG. 1 is a view illustrating a configuration of an endoscope processing apparatus according to a first embodiment.

Hereinafter, preferred embodiments of the present invention will be described with reference to drawings. Note that, in each of the drawings to be used in the description below, in order to show each of the components in a recognizable size, scale sizes are made different for each of the components. The present invention is not limited only to the number, shape, size ratio of the components and relative positional relationship among the components which are shown in the drawings.

(First Embodiment)

An example of the present embodiment of the present invention will be described below. An endoscope processing apparatus 1 according to the present embodiment as shown in FIG. 1 is schematically an apparatus that performs at least one of a cleaning processing and a disinfection processing on at least one of an endoscope and endoscope accessories housed in a cleaning tank 2, by using a mixed liquid obtained by mixing a plurality of liquids.

In the present embodiment, as one example, the endoscope processing apparatus 1 is configured to be able to perform on at least one of an endoscope and endoscope accessories the cleaning processing by using two-phase gas-liquid flow obtained by mixing the mixed liquid and gas at a predetermined ratio.

Note that the composition of a plurality of liquids for generating a mixed liquid and the mixing ratio of the plurality of liquids are not particularly limited. In addition, the form of supplying the plurality of liquids into the endoscope processing apparatus 1 is determined appropriately depending on a kind or a used amount of each of the liquids, and is not particularly limited. For example, the plurality of liquids may be supplied from a supply equipment provided outside the endoscope processing apparatus 1, may be supplied from a storage tank fixed to the endoscope processing apparatus 1, or may be supplied from a container such as a bottle which is attachable to and detachable from the endoscope processing apparatus 1.

In the present embodiment, as one example, the plurality of liquids are composed of two kinds of liquids, that is, tap water as a first liquid and a medicinal solution as a second liquid, and the mixed liquid is obtained by mixing the water and the medicinal solution at a predetermined volume ratio.

As shown in FIG. 1, the tap water is supplied at a substantially constant pressure from a water facility 23 provided outside the endoscope processing apparatus 1. The water facility 23 is connected to a first-liquid introducing section 20, to be described later, provided in the endoscope processing apparatus 1. The tap water as the first liquid is introduced into the endoscope processing apparatus 1 via the first-liquid introducing section 20.

The medicinal solution is stored in a medicinal solution storage tank 33 detachably disposed to the endoscope processing apparatus 1. The medicinal solution storage tank 33 is connected to a second-liquid introducing section 30, to be described later, provided in the endoscope processing apparatus 1. The medicinal solution as the second liquid is introduced into the endoscope processing apparatus 1 via the second-liquid introducing section 30.

The endoscope processing apparatus 1 is configured by mainly including a control section 3, a cleaning tank 2, a multipurpose conduit 10, the first-liquid introducing section 20, the second-liquid introducing section 30, a liquid-feeding section 40, a stiffing conduit 60, and a gas-liquid mixing section 70.

The control section 3 is an apparatus that controls operations of the respective components, to be described later, of the endoscope processing apparatus 1 based on a predetermined program, and is configured by a computer including a calculating device, a memory device, an auxiliary memory device, an input/output device and the like, for example. In addition, though not shown in the drawings, the endoscope processing apparatus 1 is provided with a power supply device that supplies power to the control section 3 and other components of the endoscope processing apparatus 1.

The cleaning tank 2 is a container which is able to house inside thereof an endoscope 100 or endoscope accessories (not shown). The cleaning tank 2 includes inside thereof a discharge port 11, a liquid drainage port 12 and a liquid inlet port 13. Note that the cleaning tank 2 may have a sealable structure with an openable/closable lid member so as to prevent the liquid inside the tank from spilling outside. Note that one endoscope 100 is housed in the cleaning tank 2 in the drawings, but the cleaning tank 2 may be configured to be able to house inside thereof a plurality of endoscopes 100.

Though not shown in the drawings, the cleaning tank 2 is appropriately provided with a holding section for holding the endoscope 100 and endoscope accessories in a predetermined posture, a temperature measuring section for measuring a temperature of the liquid in the cleaning tank 2, and a temperature adjusting section for maintaining the temperature of the liquid in the cleaning tank 2 at a predetermined value, for example.

The discharge port 11 is an opening portion provided in the cleaning tank 2. The discharge port 11 is connected to the gas-liquid mixing section 70, to be described later, through a discharge conduit 71. The discharge port 11 is used for sending fluid delivered from the gas-liquid mixing section 70 into a conduit, not shown, such as a treatment instrument channel provided in the endoscope 100. In the present embodiment, the discharge port 11 is connected to the conduit of the endoscope 100 through a connecting tube 101.

In addition, in the present embodiment, the discharge port 11 is provided with a discharge valve 11a which is an electromagnetic valve for opening and closing the discharge port 11, as one example. Though not shown in the drawings, the discharge valve 11a is electrically connected to the control section 3 and configured to open and close in response to an output signal from the control section 3.

Note that one discharge port 11 is shown in the drawings, but a plurality of discharge ports 11 may be provided in the cleaning tank 2. When a plurality of discharge ports 11 are provided in the cleaning tank 2, for example, a plurality of discharge valves 11a are disposed so as to be able to independently open and close the respective discharge ports 11.

The gas-liquid mixing section 70, though details thereof will be described later, mixes the gas delivered from an air-feeding section 72 and the liquid delivered from a liquid-feeding section 40 at a predetermined ratio to generate a two-phase gas-liquid flow, and discharges the two-phase gas-liquid flow from the discharge port 11 through the discharge conduit 70.

The liquid drainage port 12 is an opening portion provided in the cleaning tank 2. The liquid drainage port 12 is connected to a liquid drainage conduit 80. The liquid drainage port 12 is used for draining the liquid in the cleaning tank 2 outside the cleaning tank 2 through the liquid drainage conduit 80.

The configuration for draining the liquid in the cleaning tank 2 outside the cleaning tank 2 through the liquid drainage port 12 and the liquid drainage conduit 80 is not particularly limited. In the present embodiment, as one example, the liquid drainage port 12 is disposed at the lowest position of the bottom surface of the cleaning tank 2 and the liquid drainage conduit 80 is provided with a liquid drainage valve 81 which is an electromagnetic valve. Though not shown in the drawings, the liquid drainage valve 81 is electrically connected to the control section 3 and configured to open and close in response to an output signal from the control section 3.

In the endoscope processing apparatus 1 according to the present embodiment, when the liquid drainage valve 81 is brought into an open state, the liquid in the cleaning tank 2 is drained outside the cleaning tank 2 by gravity through the liquid drainage port 12 and the liquid drainage conduit 80. Note that the endoscope processing apparatus 1 may be provided with an electric pump for sucking the liquid in the cleaning tank 2 to drain the liquid outside the cleaning tank 2.

The liquid inlet port 13 is an opening portion provided in the cleaning tank 2. The liquid inlet port 13 is connected to the multipurpose conduit 10, to be described later. The liquid inlet port 13 is configured to allow bi-directional passage of fluid, that is, in a direction from inside the cleaning tank 2 toward inside the multipurpose conduit 10, and in a direction from the multipurpose conduit 10 toward inside the cleaning tank 2. Furthermore, the liquid inlet port 13 is configured to prevent the liquid delivered into the cleaning tank 2 from entering again into the multipurpose conduit 10 through the liquid inlet port 13, when liquid is drained from the liquid drainage port 12 and also liquid is delivered from the multipurpose conduit 10 into the cleaning tank 2 through the liquid inlet port 13.

The configuration for preventing the liquid delivered once from the liquid inlet port 13 from flowing back into the liquid inlet port 13 at the time of drainage of the liquid from the liquid drainage port 12 is not particularly limited. In the present embodiment, as one example, the liquid inlet port 13 is configured to open at an upper position than the bottom surface of the cleaning tank 2 by a predetermined height, thereby preventing the liquid delivered from the liquid inlet port 13 from flowing back.

More particularly, in the present embodiment, the liquid inlet port 13 opens at a position higher than the position of the liquid drainage port 12 in a substantially upward direction. According to such a configuration, when the liquid drainage valve 81 is in an open state, all the liquids delivered from the liquid inlet port 13 are drained from inside the cleaning tank 2 through the liquid drainage port 12. Therefore, the liquid delivered from the liquid inlet port 13 does not flow back inside the liquid inlet port 13.

Note that the configuration for preventing the liquid delivered from the liquid inlet port 13 from flowing back is not limited to the present embodiment, and can be implemented also with a configuration in which an electromagnetic valve is provided to the liquid inlet port 13 and the electromagnetic valve is brought into an open state only when a liquid is delivered from the liquid inlet port 13, for example.

In addition, in the present embodiment, the liquid inlet port 13 is provided with a filter 14 that filters the liquid passing through the liquid inlet port 13, as one example.

The multipurpose conduit 10 is a hollow member having a predetermined capacity n. In the present embodiment, the capacity n of the multipurpose conduit 10 has a value larger than the volume of the mixed liquid which is necessary for performing a two-phase gas-liquid flow cleaning processing to be described later.

The multipurpose conduit 10 is connected to the cleaning tank 2 through the liquid inlet port 13, as described above. The liquid inlet port 13 is provided at the uppermost position of the multipurpose conduit 10. In other words, in the endoscope processing apparatus 1 according to the present embodiment, the uppermost position of the multipurpose conduit 10 is connected to the cleaning tank 2 at the position higher than the position of the liquid drainage port 12 through the liquid inlet port 13.

Note that the shape of the multipurpose conduit 10 is not particularly limited, and is appropriately selected depending on various conditions such as a size of the endoscope processing apparatus, and a balance with other components. The multipurpose conduit 10 may be a tubular member as shown in FIG. 1, for example, or may be a container-like member having a substantially rectangular parallelepiped shape or a substantially globe shape. In addition, the multipurpose conduit 10 may be made of a flexible material and configured to be bendable so as to avoid interference with other components in the internal space of the endoscope processing apparatus 1.

As shown in FIG. 1, the multipurpose conduit 10 is connected with the first-liquid introducing section 20, the second-liquid introducing section 30, the liquid-feeding section 40 and the stirring conduit 60, in addition to the above-described cleaning tank 2.

The first-liquid introducing section 20 is used for introducing the first liquid into the multipurpose conduit 10. In the present embodiment, the first liquid is tap water as described above, and the first-liquid introducing section 20 is connected to the water facility 23 provided outside the endoscope processing apparatus 1.

The first-liquid introducing section 20 includes a water supply conduit 21 that connects the water facility 23 and the multipurpose conduit 10 and a water supply valve 22 as an electromagnetic valve that opens and closes the water supply conduit. Though not shown in the drawings, the water supply valve 22 is electrically connected to the control section 3, and is configured to open and close the water supply conduit 21 in response to an output signal from the control section 3. That is, when the water supply valve 22 is brought into an open state, the tap water is introduced into the multipurpose conduit 10.

Note that the first-liquid introducing section 20 is appropriately provided with a pressure adjusting section for maintaining the pressure of the tap water supplied from the water facility 23 at a predetermined value, and an orifice for maintaining the flow rate of the tap water at a predetermined value, and the like.

In addition, if the first liquid is not supplied at a predetermined pressure as in the case of the tap water, but is stored in a container to be supplied as in the case of distilled water and a medicinal solution, for example, the first-liquid introducing section 20 is configured to introduce the first liquid stored in the container into the multipurpose conduit 10 using an electromagnetic pump.

The second-liquid introducing section 30 is used for introducing the second liquid into the multipurpose conduit 10. In the present embodiment, the second liquid is the medicinal solution stored in the medicinal solution storage tank 33 as described above, and the second-liquid introducing section 30 is connected to the medicinal solution storage tank 33.

The second-liquid introducing section 30 includes a medicinal solution supply conduit 31 that connects the medicinal solution storage tank 33 and the multipurpose conduit 10, and a medicinal solution pump 32 as an electric pump that transfers the fluid in the medicinal solution supply conduit 31 from the medicinal solution storage tank 33 toward the multipurpose conduit 10. Though not shown in the drawings, the medicinal solution pump 32 is electrically connected to the control section 3 and configured to operate in response to an output signal from the control section 3. In addition, the medicinal solution pump 32, when operated, is configured to transfer a substantially constant flow rate of medicinal solution toward inside of the multipurpose conduit 10. That is, in the present embodiment, the medicinal solution pump 32 is operated, thereby introducing the medicinal solution of a predetermined volume into the multipurpose conduit 10 per unit time.

Note that, when the second liquid is supplied at a predetermined pressure by an equipment such as a pump provided outside the endoscope processing apparatus 1, the second-liquid introducing section 30 is configured by including an electromagnetic valve instead of the medicinal solution pump 32.

The liquid-feeding section 40 and the stirring conduit 60 connect the multipurpose conduit 10 and the gas-liquid mixing section 70. The liquid-feeding section 40 is used for transferring the liquid in the multipurpose conduit 10 to the gas-liquid mixing section 70.

The configuration of the liquid-feeding section 40 is not particularly limited, as long as the liquid-feeding section is capable of transferring the liquid in the multipurpose conduit 10 to the gas-liquid mixing section 70. In the present embodiment, as one example, the liquid-feeding section 40 includes: a liquid-feeding conduit 41 and a TPF conduit 51 that connect the multipurpose conduit 10 and the gas-liquid mixing section 70; a liquid-feeding pump 42 as an electric pump that transfers the fluid in the liquid-feeding conduit 41 from the multipurpose conduit 10 to the gas-liquid mixing section 70; and a TPF pump 52 as an electric pump that transfers the fluid in the TPF conduit 51 from the multipurpose conduit 10 to the gas-liquid mixing section 70.

Though not shown in the drawings, the liquid-feeding pump 42 and the TPF pump 52 are electrically connected to the control section 3, and configured to independently operate in response to output signals from the control section 3.

In the present embodiment, the TPF pump 52 is configured to be able to accurately transfer a liquid at a relatively small flow rate. In addition, the liquid-feeding pump 42 can transfer a liquid at a larger flow rate than the TPF pump 52.

Note that the liquid-feeding section 40 may include only one conduit and one electric pump arranged to the one conduit and capable of changing the flow rate. In this case, it is preferable that the electric pump provided to the liquid-feeding section 40 is capable of changing the flow rate. In addition, as described later, when liquid is stirred between the multipurpose conduit 10 and the gas-liquid mixing section 70 using the liquid-feeding section 40 configured by one conduit and one electric pump, it is preferable that the electric pump is rotatable forward and reversely.

The air-feeding section 72 includes a compressor 73 and the air-feeding conduit 74 that connects the compressor 73 and the gas-liquid mixing section 70. The compressor 73 is configured to deliver air at a predetermined pressure and a predetermined flow rate in the present embodiment, as one example. Though not shown in the drawings, the compressor 73 is electrically connected to the control section 3 and configured to operate in response to an output signal from the control section 3.

In addition, the air-feeding conduit 74 is provided with a check valve 75. The check valve 75 is configured to restrict the flowing direction of the fluid in the air-feeding conduit 74 only to the direction from the compressor 73 toward the gas-liquid mixing section 70.

Note that the compressor may be provided outside the endoscope processing apparatus 1 and may be configured to deliver air constantly at a predetermined pressure and flow rate. In this case, the endoscope processing apparatus 1 is provided with an electromagnetic valve for opening and closing the air-feeding conduit 74 connected to the compressor.

The stirring conduit 60 is a conduit for connecting the gas-liquid mixing section 70 and the multipurpose conduit 10 and transferring the liquid from the gas-liquid mixing section 70 toward the multipurpose conduit 10. The stiffing conduit 60 may be provided with an opening/closing section 61 as an electromagnetic valve for opening and closing the stirring conduit 60. If the liquid-feeding section 40 is configured to stir the liquid, the stiffing conduit 60 may be provided with the opening/closing section 61 or not. Through not shown in the drawings, the opening/closing section 61 is electrically connected to the control section 3 and configured to open and close in response to an output signal from the control section 3.

The gas-liquid mixing section 70 is connected to the liquid-feeding section 40, the air-feeding section 72 and the discharge port 11, as described above. The gas-liquid mixing section 70 is configured to mix the gas delivered from the air-feeding section 72 and the liquid delivered from the liquid-feeding section 40 to generate a two-phase gas-liquid flow (TPF) to deliver the two-phase gas liquid flow to the discharge conduit 71.

Note that, when a liquid is introduced from the liquid-feeding section 40 to the gas-liquid mixing section 70, and the discharge valve 11a is in an open state and the opening/closing section 61 is in a closed state, the gas-liquid mixing section 70 delivers the liquid to the discharge conduit 71. In addition, when a liquid is introduced from the liquid-feeding section 40 to the gas-liquid mixing section 70, and the discharge valve 11a is in a closed state and the opening/closing section 61 is in an open state, the gas-liquid mixing section 70 delivers the liquid to the stiffing conduit 60.

Furthermore, in addition to the components described above, the endoscope processing apparatus 1 is provided with a disinfectant solution introducing section that introduces a disinfectant solution for performing disinfection processing on the conduits and the endoscope 100 of the endoscope processing apparatus 1 into the cleaning tank 2.

Figure 8:
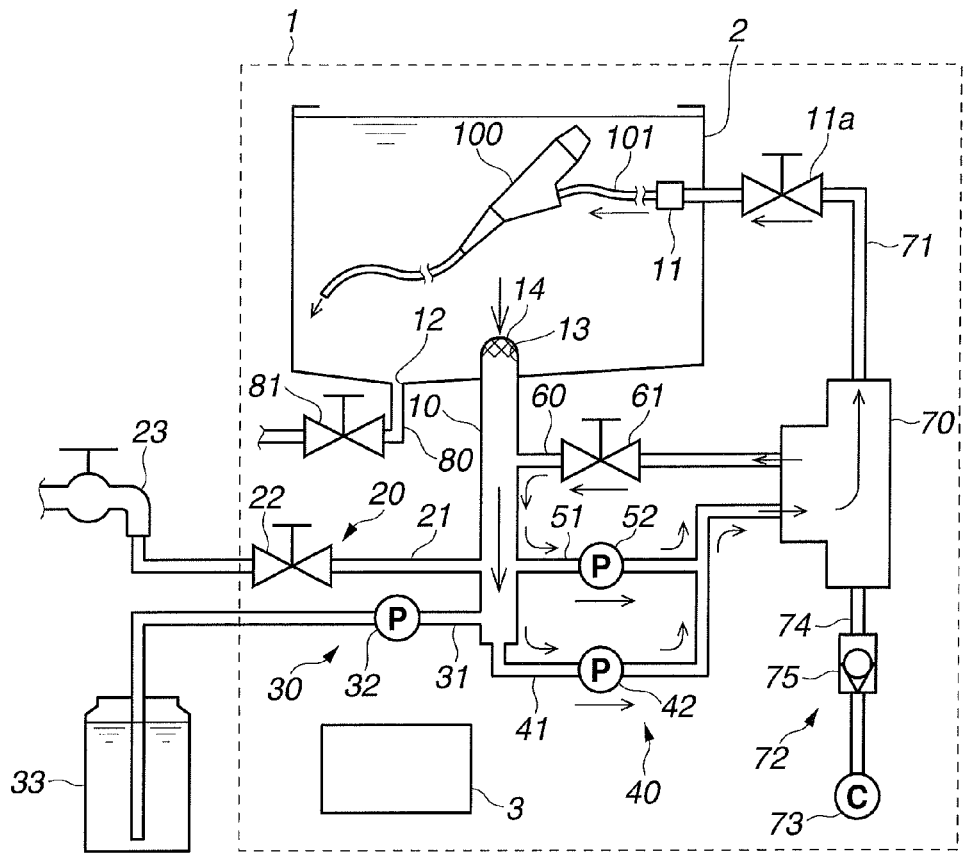
FIG. 8 is a view illustrating a disinfection process.
Figure 9:
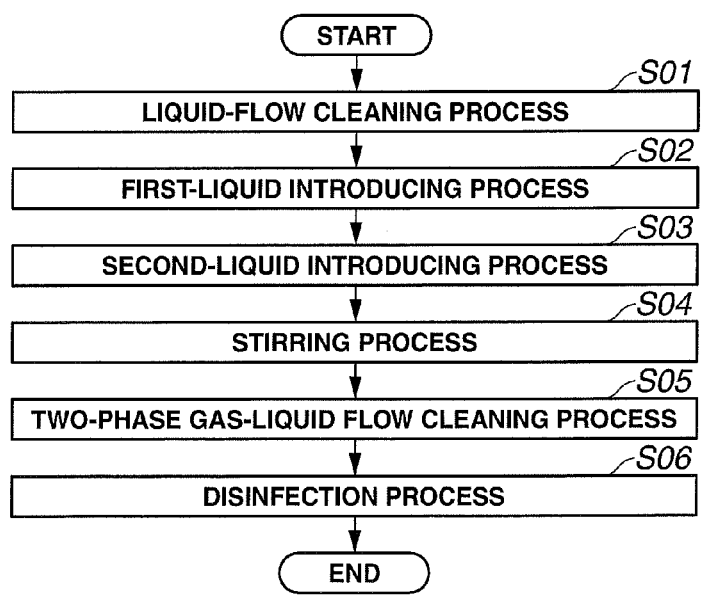
FIG. 9 is a flowchart of a processing performed by the endoscope processing apparatus.

The operation of the endoscope processing apparatus 1 having the configuration as described above will be described with reference to FIGS. 2 to 8 and the flowchart shown in FIG. 9. Note that, at the time that the operation shown in the flowchart in FIG. 9 is started, it is supposed that the endoscope 100 has already been housed in the cleaning tank 2 and the conduit of the endoscope 100 is connected to the discharge port 11 via a connecting conduit 101. In addition, at the time that the operation shown in the flowchart in FIG. 9 is started, it is supposed that the medicinal solution pump 32, the liquid-feeding pump 42, the TPF pump (two-phase gas-liquid flow pump) 52, and the compressor 73 are in an operation-stopped state, and the discharge valve 11a, the opening/closing section 61 and the drainage valve 81 are in a closed state.

Figure 2:
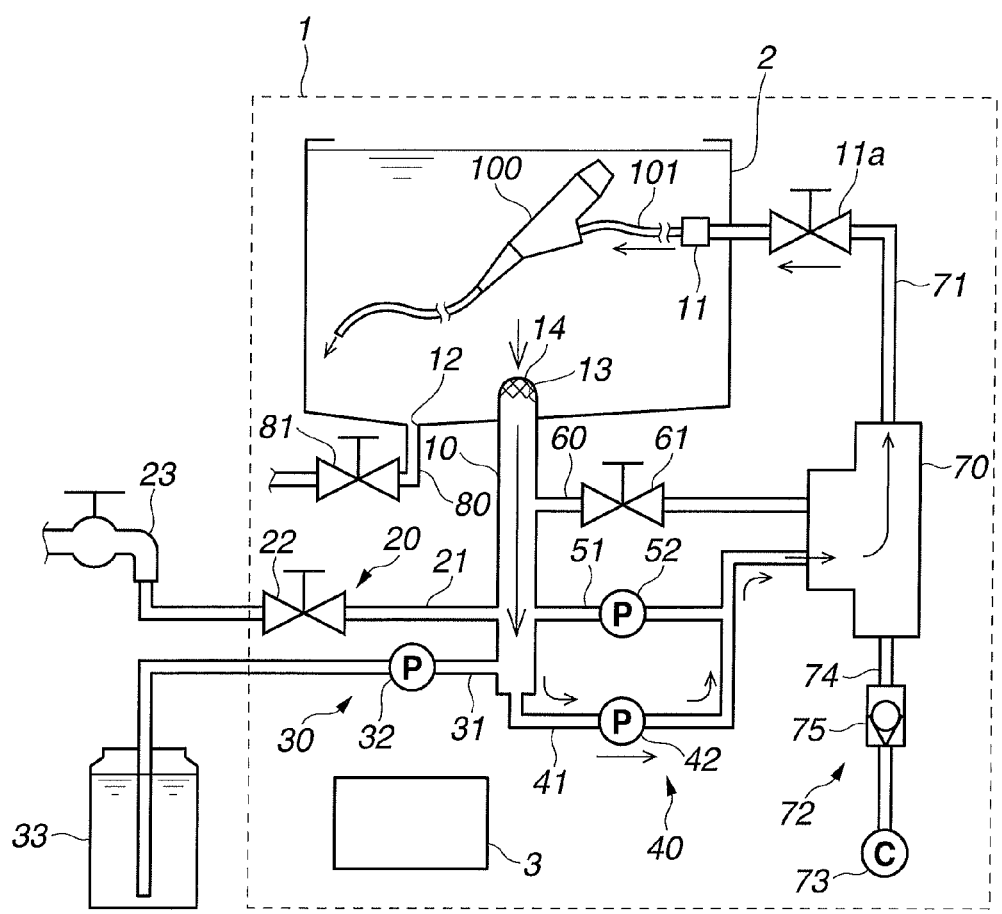
FIG. 2 is a view illustrating a liquid-flow cleaning process.

First, in a step S01, a liquid-flow cleaning process is performed, in which extraneous substances adhering to the endoscope 100 are washed away with a liquid composed of at least one of tap water and a cleaning agent. In the step S01, as shown in FIG. 2, a cleaning agent as a liquid is filled in the cleaning tank 2, and thereafter the discharge port 11 is brought into an open state and the liquid-feeding pump 42 is operated.

The liquid-feeding pump 42 is operated, thereby causing the cleaning agent in the cleaning tank 2 to circulate so as to enter the multipurpose conduit 10 through the liquid inlet port 13, pass through the liquid-feeding conduit 41, the gas-liquid mixing section 70, the discharge conduit 71, the discharge port 11, and the conduit of the endoscope 100, and then return to the cleaning tank 2. The circulation of the cleaning agent washes away extraneous substances which are easy to come off among the extraneous substances adhering to inside the conduit of the endoscope 100. In addition, among the extraneous substances washed away by the circulation of the cleaning agent, relatively large extraneous substances are caught by the filter 14 and adhere to the side of the cleaning tank 2 of the filter 14.

Figure 3:
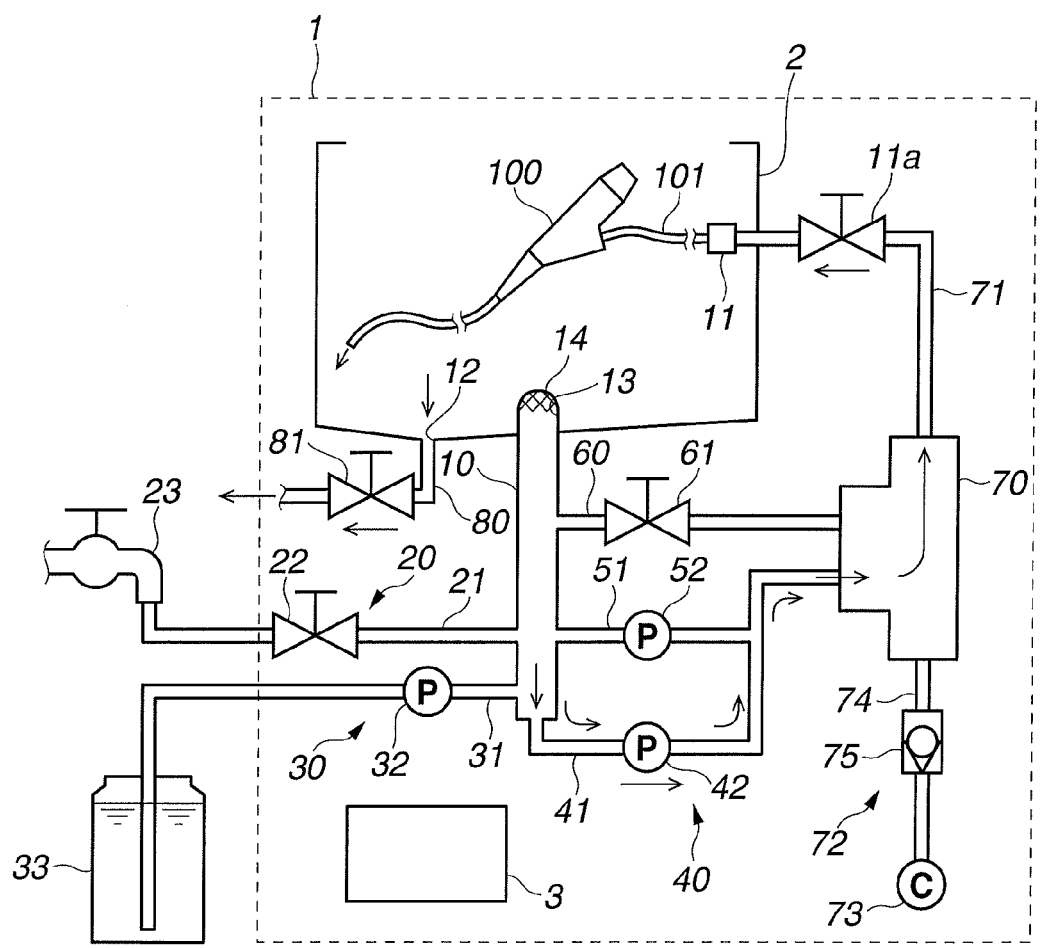
FIG. 3 is a view illustrating a method of draining a liquid from a cleaning tank.

After the cleaning agent is circulated by operating the liquid-feeding pump 42 for a predetermined time period, the drainage valve 81 is brought into an open state to drain the cleaning agent, as shown in FIG. 3. The liquid-flow cleaning process may be performed repeatedly a plural number of times.

Figure 4:
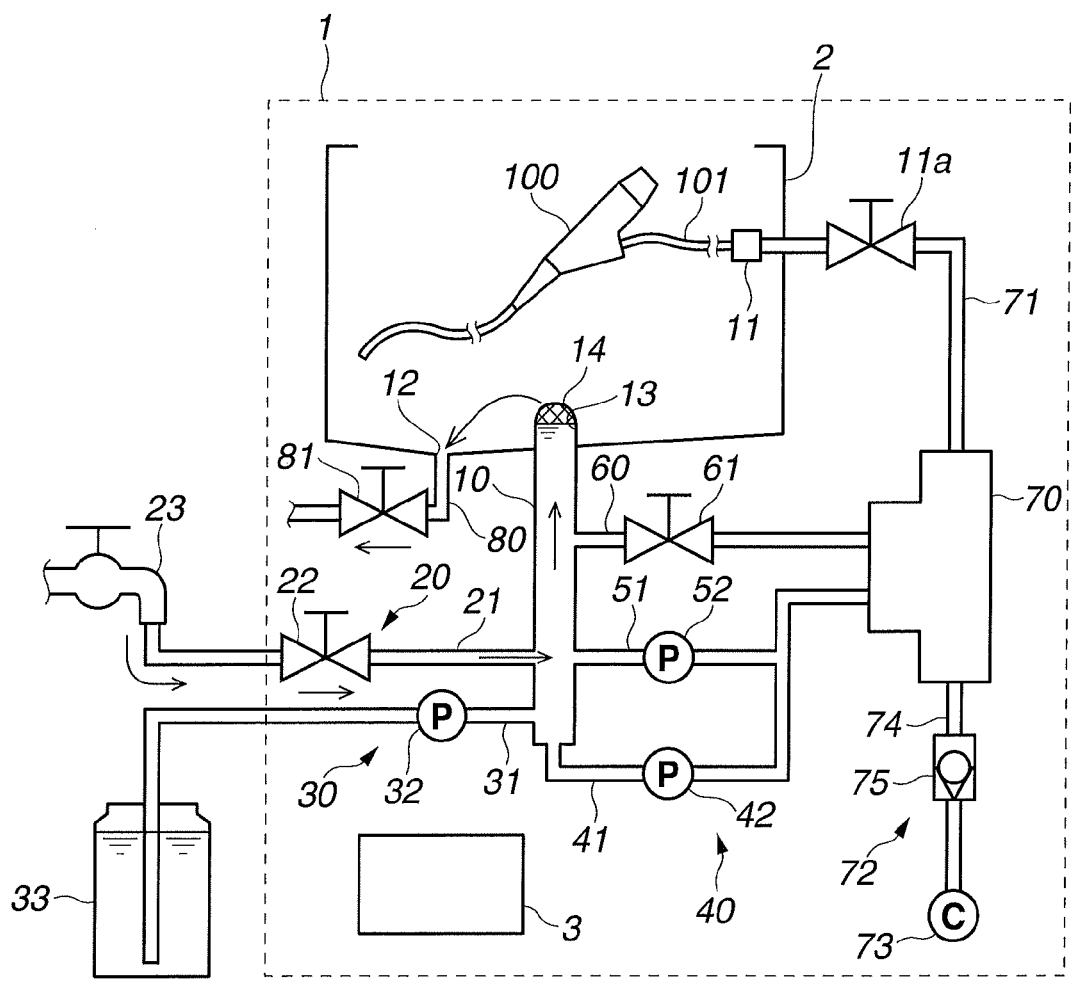
FIG. 4 is a view illustrating a first-liquid introducing process.

Next, in the step S02, a first-liquid introducing process is performed, in which tap water as the first liquid is introduced into the multipurpose conduit 10 through the first-liquid introducing section 20. In the step S02, the drainage valve 81 and the water supply valve 22 are brought into an open state, as shown in FIG. 4. Then, the water supply valve 22 is continued to be in the open state until the tap water flows out from the liquid inlet port 13 into the cleaning tank 2. After the tap water flows out from the liquid inlet port 13, the water supply valve 22 is brought into a closed state. In the present embodiment, as one example, the water supply valve 22 is continued to be in the open state only for a time period long enough for the inside the multipurpose conduit 10 having a predetermined capacity to be filled with the tap water supplied from the water facility 23 at a predetermined flow rate.

The liquid inlet port 13 is provided at the uppermost position of the multipurpose conduit 10. Therefore, when the tap water flows out from the liquid inlet port 13, inside the multipurpose conduit 10 is filled with the tap water. That is, by performing the process in step S02, the tap water of a predetermined volume n corresponding to the capacity of the multipurpose conduit 10 is stored inside the multipurpose conduit 10.

Note that the control method of opening and closing the water supply valve 22 in the step S02 is not limited to the configuration in which control is performed on the basis of time. For example, the control method may have a configuration in which a sensor for detecting a presence of liquid is provided to the liquid inlet port 13, for example, and the water supply valve 22 is brought into the closed state after directly detecting that the tap water flows out from the liquid inlet port 13. Alternatively, the control method may have a configuration in which a flow rate sensor is provided to the water supply conduit 21, for example, and the water supply valve 22 is brought into the closed state, after detecting that the tap water of a volume larger than the capacity of the multipurpose conduit 10 is introduced into the multipurpose conduit 10.

In addition, in the step S02, the tap water flowed out from the liquid inlet port 13 flows in the direction opposite to the direction of the cleaning agent flowed in the step S01. Therefore, the extraneous substances adhering to the side of the cleaning tank 2 of the filter 14 in the step S01 are removed from the filter 14 with the tap water flowed out from the liquid inlet port 13 to be swept away to the liquid drainage conduit 80.

The extraneous substances caught by the filter 14 in the liquid-flow cleaning process in the step S01 are thus removed from the filter 14 to be drained outside the endoscope processing apparatus 1 through the liquid drainage conduit 80 in the step S02. That is, the process in the step S02 is performed, thereby automatically cleaning the filter 14. As a result, the cleaning interval by a user can be prolonged, which can reduce a burden on the user.

Figure 5:
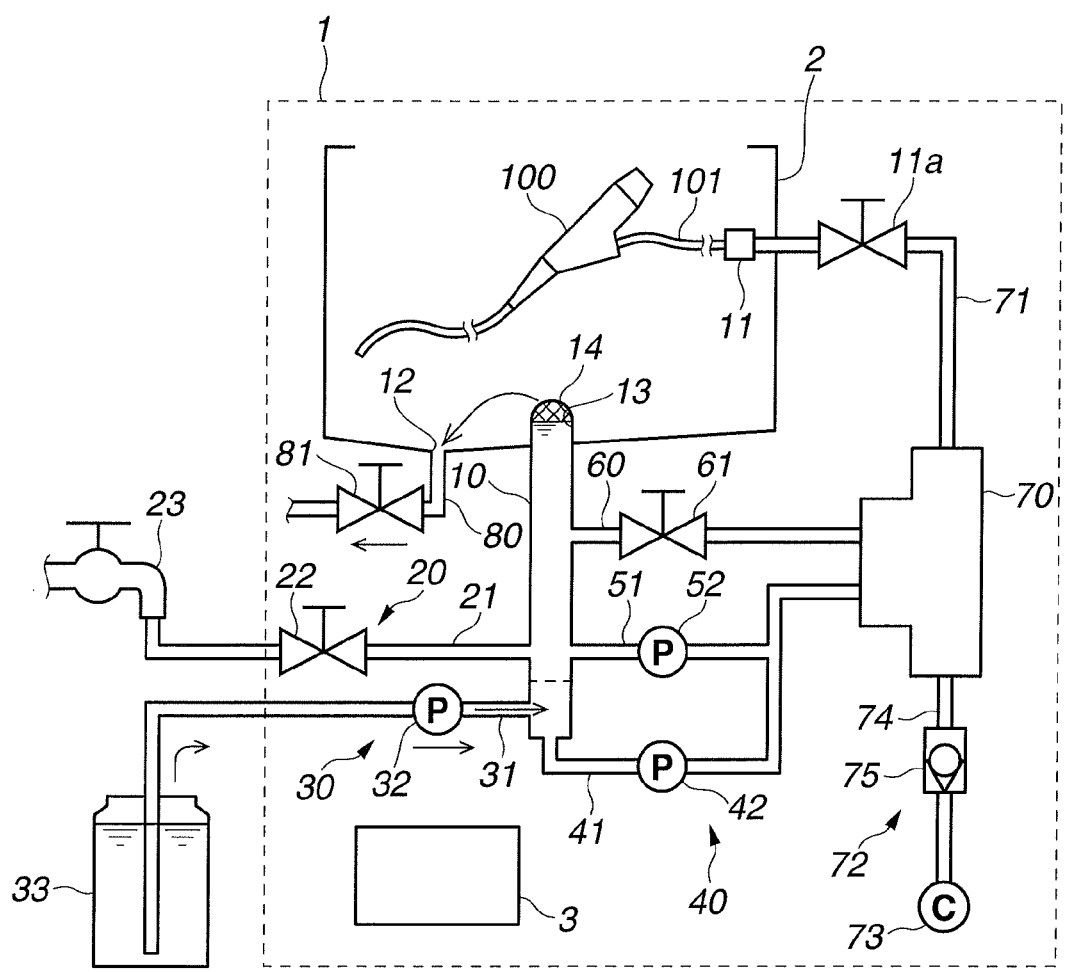
FIG. 5 is a view illustrating a second-liquid introducing process.

Next, in the step S03, a second-liquid introducing process is performed, in which a medicinal solution as the second liquid is introduced into the multipurpose conduit 10 through the second-liquid introducing section 30. In the step S03, the drainage valve 81 is brought into the open state, as shown in FIG. 5. Then, the medicinal solution pump 32 is operated only for a predetermined time period, thereby introducing the medicinal solution of a predetermined volume m into the multipurpose conduit 10.

Then, the medicinal solution is introduced into the multipurpose conduit 10, which causes the tap water of the volume which is equal to the volume m of the introduced medicinal solution to flow out from the liquid inlet port 13 toward the cleaning tank 2. Therefore, execution of the process in the step S03 causes the tap water and the medicinal solution to be stored at the volume ratio of (n-m): m in the multipurpose conduit 10.

Figure 6:
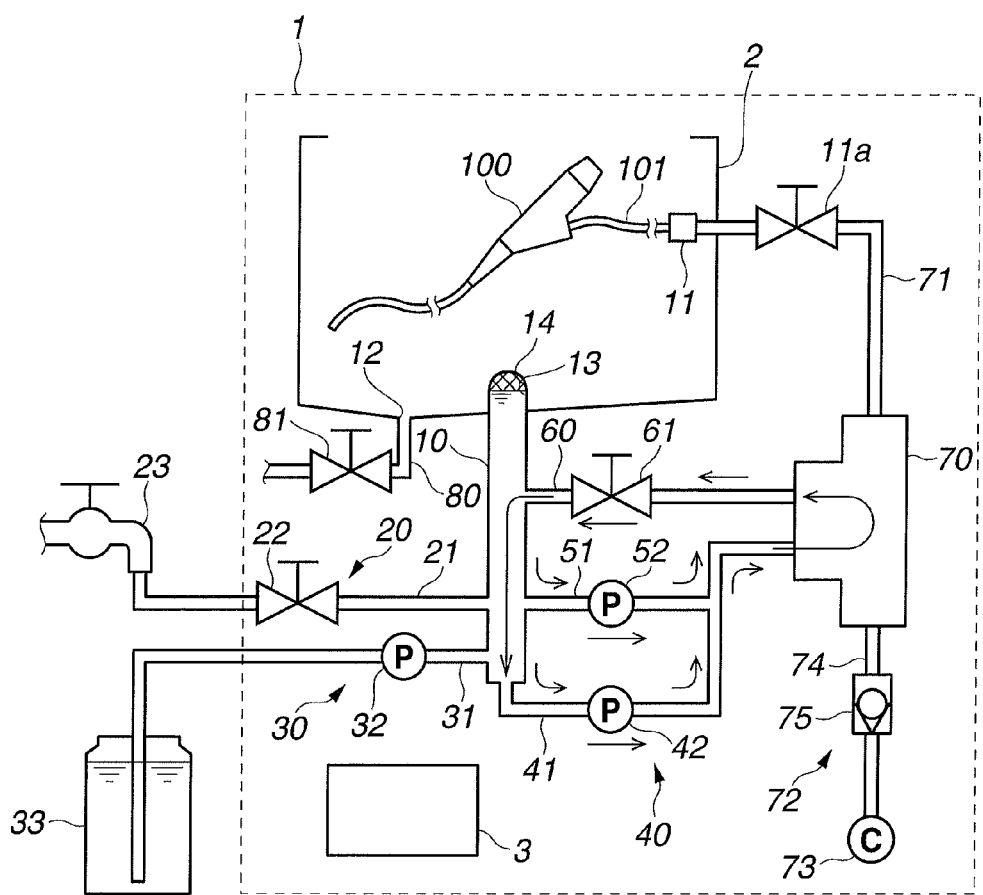
FIG. 6 is a view illustrating a stirring process.

Next, in the step S04, a stirring process is performed, in which the liquid in the multipurpose conduit 10 is stirred. In the step S04, as shown in FIG. 6, the discharge valve 11a is brought into the closed state and the opening/closing section 61 is brought into the open state, and thereafter the liquid-feeding pump 42 is operated only for a predetermined time period. At this time, in addition to the liquid-feeding pump 42, the TPF pump 52 may be operated.

In the step S04, the liquid-feeding pump 42 and the TPF pump 52 are operated, which causes the mixed liquid in the multipurpose conduit 10 to be transferred to the gas-liquid mixing section 70 through the liquid-feeding conduit 41 and the TPF conduit (two-phase gas-liquid flow conduit) 51. In this case, since the discharge valve 11a is in the closed state and the opening/closing section 61 is in the open state, the mixed liquid flows from the gas-liquid mixing section 70 into the stirring conduit 60, to return to the multipurpose conduit 10 again.

As exemplified in FIG. 6, when the liquid-feeding section 40 is provided with a plurality of conduits and each of the conduits is provided with a pump, it is possible to circulate the liquid between the multipurpose conduit 10 and the gas-liquid mixing section 70 by using these conduits without using the opening/closing section 61. For example, the liquid may be introduced from the multipurpose conduit 10 into the gas-liquid mixing section 70 using the liquid-feeding conduit 41 and the liquid-feeding pump 42, and introduced from the gas-liquid mixing section 70 to the multipurpose conduit 10 using the TPF conduit 51 and the TPF pump 52, or the order may be reversed.

When the liquid is thus stirred using the liquid-feeding section 40 without using the opening/closing section 61, if taking FIG. 6 as an example, it is preferable that the pump used for introducing the liquid from the gas-liquid mixing section 70 to the multipurpose conduit 10 is rotatable forward and reversely.

The liquid is circulated and stirred, thereby capable of reducing unevenness in the liquid temperature and uniformly dispersing the mixed materials included in the liquid.

Execution of the process in the step S04 causes the mixed liquid of the tap water and the medicinal solution stored in the multipurpose conduit 10 to be stirred and substantially uniformly mixed. As described above, the volume ratio of the tap water to the medicinal solution in the mixed liquid is (n-m): m. In the present embodiment, the volume m of the medicinal solution can be changed within a range not exceeding the volume n of the tap water by the operation time period of the medicinal solution pump 32 in the step S03. Therefore, the endoscope processing apparatus 1 according to the present embodiment can generate a mixed liquid in which the tap water and the medicinal solution are mixed at an arbitrary ratio.

Figure 7:
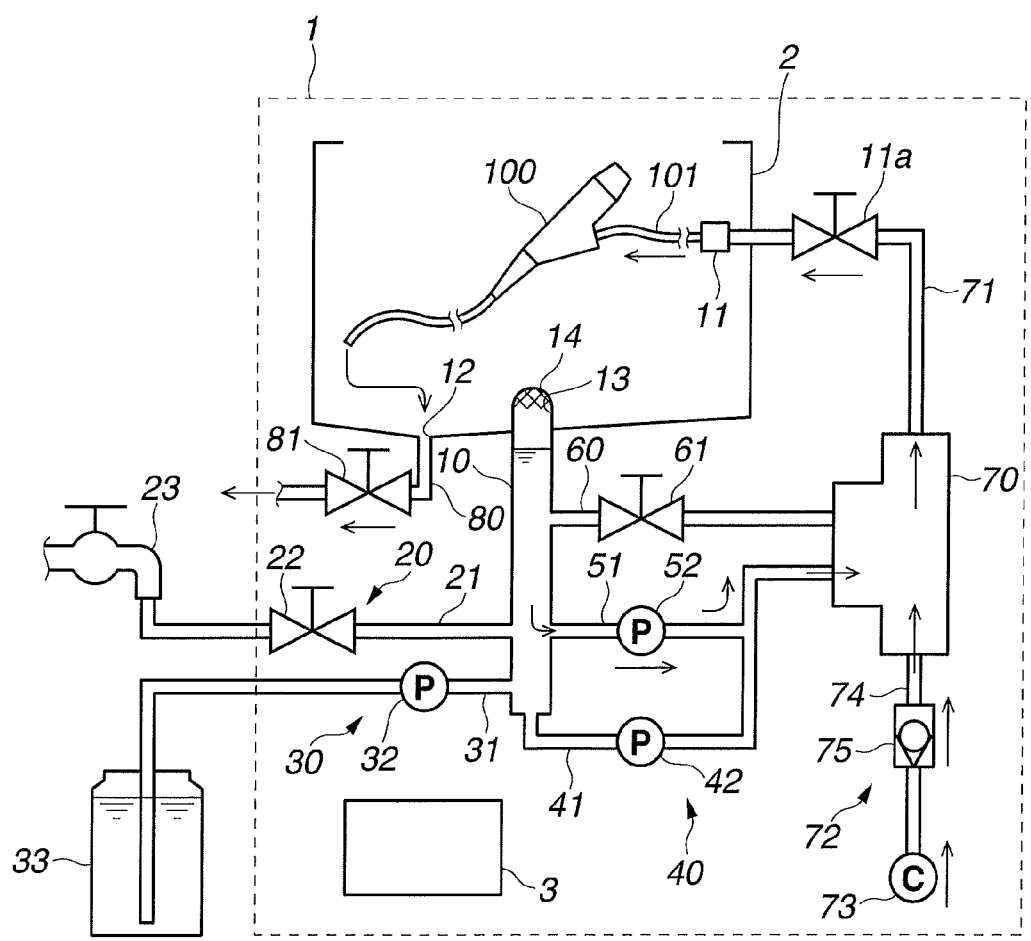
FIG. 7 is a view illustrating a two-phase gas-liquid flow cleaning process.

Next, in the step S05, a two-phase gas-liquid flow cleaning process is performed, in which the inside of the conduit of the endoscope 100 is cleaned with two-phase gas-liquid flow obtained by mixing air and mixed liquid. In the step S05, as shown in FIG. 7, the discharge valve 11a and the drainage valve 81 are brought into the open state and the opening/closing section 61 is brought into the closed state. Then, the compressor 73 and the TPF pump 52 are operated only for a predetermined time period.

In the step S05, the compressor 73 is operated, thereby causing air of a predetermined flow rate to be introduced into the gas-liquid mixing section 70 through the air-feeding conduit 74. In addition, the TPF pump 52 is operated, thereby causing the mixed liquid in the multipurpose conduit 10 to be introduced into the gas-liquid mixing section 70 at a predetermined flow rate through the TPF conduit 51.

Then, the two-phase gas-liquid flow obtained by mixing air and mixed liquid at a predetermined ratio is generated in the gas-liquid mixing section 70. The two-phase gas-liquid flow passes through the discharge conduit 71, the discharge port 11 and the connecting conduit 101, to be introduced into the endoscope 100. That is, inside the conduit of the endoscope 100 is cleaned with the two-phase gas-liquid flow.

At this time, the liquid inlet port 13 opens at a position higher than the position of the liquid drainage port 12 in the cleaning tank 2, and the drainage valve 81 is in the open state, the mixed liquid included in the two-phase gas-liquid flow used for cleaning inside of the conduit of the endoscope 100 and drained outside the conduit is drained outside the endoscope processing apparatus 1 through the liquid drainage port 12 and the liquid drainage conduit 80.

That is, in the present embodiment, the mixed liquid which has once passed through inside the conduit of the endoscope 100 and used for cleaning is drained without fail and is never used for cleaning again. Therefore, the extraneous substances washed away in the two-phase gas-liquid flow cleaning process are prevented from entering into the multipurpose conduit 10, thereby capable of preventing the extraneous substances from being caught up in the two-phase gas-liquid conduit and adhered again to the endoscope 100. In addition, the extraneous substances do not adhere to the multipurpose conduit 10 and inside of the TPF conduit 51. As a result, it is possible to make the cleaning processing in these conduits simple.

Next, in the step S06, a disinfection process is performed, in which disinfection processing is performed on the endoscope 100 and the endoscope processing apparatus 1. In the step S06, as shown in FIG. 8, inside of the cleaning tank 2 is filled with a disinfectant solution, with the drainage valve 81 being in the closed state and the opening/closing section 61 and the discharge valve 11a being in the open state. Then, the liquid-feeding pump 42 and the TPF pump 52 are operated.

In the step S06, the liquid-feeding pump 42 and the TPF pump 52 are operated, thereby causing the disinfectant solution in the cleaning tank 2 to circulate so as to enter into the multipurpose conduit 10 through the liquid inlet port 13, pass through the liquid-feeding conduit 41, the TPF conduit 51, the gas-liquid mixing section 70, the discharge conduit 71, the discharge port 11 and the conduit of the endoscope 100, to return into the cleaning tank 2. In addition, the opening/closing section 61 is in the open state, a part of the disinfectant solution flows from the gas-liquid mixing section 70 into the stirring conduit 60 to return into the multipurpose conduit 10 again.

The endoscope 100 is soaked in the disinfectant solution in the cleaning tank 2, and the disinfectant solution is flowed into the conduit of the endoscope 100, thereby performing the disinfection processing of the endoscope 100. At the same time, the disinfectant solution is flowed also to the cleaning tank 2, the multipurpose conduit 10, liquid-feeding conduit 41, the TPF conduit 51, the gas-liquid mixing section 70 and the stiffing conduit 60, thereby also performing the disinfection processing of the endoscope processing apparatus 1.

Thus, in the present embodiment, it is possible to automatically perform the disinfection processing of the endoscope processing apparatus 1 simultaneously with the disinfection processing of the endoscope 100, which prevents bacteria from remaining in the endoscope processing apparatus 1.

As described above, the endoscope processing apparatus 1 according to the present embodiment is an apparatus that performs the cleaning processing using the two-phase gas-liquid flow on at least one of the endoscope 100 and the endoscope accessories, and is capable of generating the mixed liquid used for the two-phase gas-liquid flow without using a mixing tank and a liquid level sensor. Therefore, in contrast to a conventional endoscope processing apparatus that generates a mixed liquid using a combination of a mixing tank and a liquid level sensor, the endoscope processing apparatus 1 according to the present embodiment has a smaller size and simpler configuration.

(Second Embodiment)

The second embodiment of the present invention will be described below. The second embodiment is different from the first embodiment in a part of the configuration for connecting the multipurpose conduit 10 and the gas-liquid mixing section 70. Only the point different from the first embodiment will be described below, and the same components as those in the first embodiment are attached with the same reference numerals and descriptions thereof will be appropriately omitted.

Figure 10:
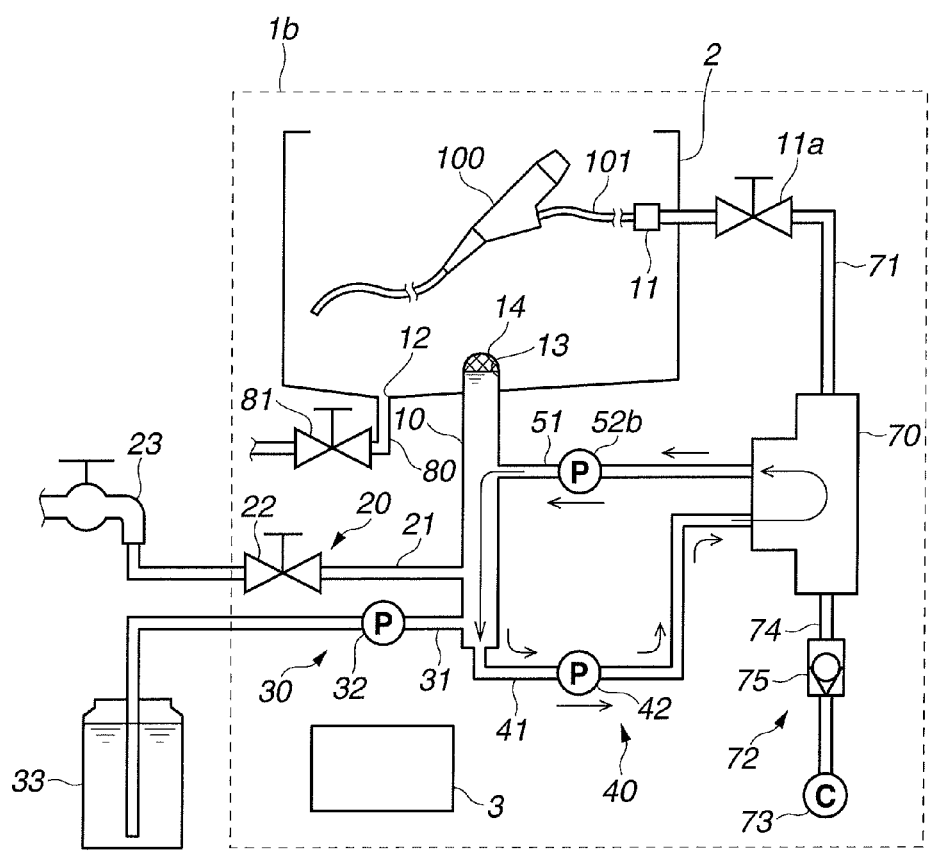
FIG. 10 is a view illustrating a configuration of an endoscope apparatus according to a second embodiment.

As shown in FIG. 10, an endoscope processing apparatus 1b according to the present embodiment is configured such that the multipurpose conduit 10 and the gas-liquid mixing section 70 are connected to each other only by the liquid-feeding section 40. That is, the stirring conduit 60 and the opening/closing section 61 provided in the endoscope processing apparatus 1 in the first embodiment are not provided in the endoscope processing apparatus 1b in the present embodiment.

In addition, the liquid-feeding section 40 according to the present embodiment is configured such that the TPF pump 52 is rotatable forward and reversely. That is, the TPF pump 52 can bi-directionally transfer the fluid in the TPF conduit 51 connecting the multipurpose conduit 10 and the gas-liquid mixing section 70.

In the endoscope processing apparatus 1b according to the present embodiment which has the configuration as described above, in the stiffing process in the step S04, the liquid-feeding pump 42 is operated such that the fluid in the liquid-feeding conduit 41 is transferred from the multipurpose conduit 10 toward the gas-liquid mixing section 70, as shown in FIG. 10. In addition, the TPF pump 52 is operated in the reverse direction such that the fluid in the TPF conduit 51 is transferred from the gas-liquid mixing section 70 toward the multipurpose conduit 10.

In the step S04, the liquid-feeding pump 42 and the TPF pump 52 are operated, thereby causing the mixed liquid in the multipurpose conduit 10 to be transferred to the gas-liquid mixing section 70 through the liquid-feeding conduit 41, and further to be transferred from the gas-liquid mixing section 70 so as to return to the multipurpose conduit 10 through the TPF conduit 51.

As described above, also with the configuration of the endoscope processing apparatus 1b according to the present embodiment, it is possible to perform the stirring process for stirring the mixed liquid of the tap water and the medicinal solution stored in the multipurpose conduit 10. Other operations of the endoscope processing apparatus 1b are the same as those in the first embodiment.

The endoscope processing apparatus 1b according to the present embodiment can be configured in a reduced size with a simpler configuration, because there is no need for providing the stirring conduit 60 and the opening/closing section 61 which are provided in the endoscope processing apparatus 1 in the first embodiment.

Note that, in the present embodiment, the TPF pump 52 is configured to be operable forward and reversely and the circulation of the mixed liquid in the stirring process is performed by operating the TPF pump 52 in the reverse direction. However, also in a case where the liquid-feeding pump 42 is configured to be operable forward and reversely, the same operation can be performed. That is, it is enough that at least one of the TPF pump 52 and the liquid-feeding pump 42 is operable forward and reversely.

(Third Embodiment)

The third embodiment of the present invention will be described below. The third embodiment is different from the first embodiment and the second embodiment in a part of the configuration for connecting the multipurpose conduit 10 and the gas-liquid mixing section 70. Only the points different from the first and second embodiments will be described below, and the same components as those in the first and second embodiments are attached with the same reference numerals and descriptions thereof will be appropriately omitted.

Figure 11:
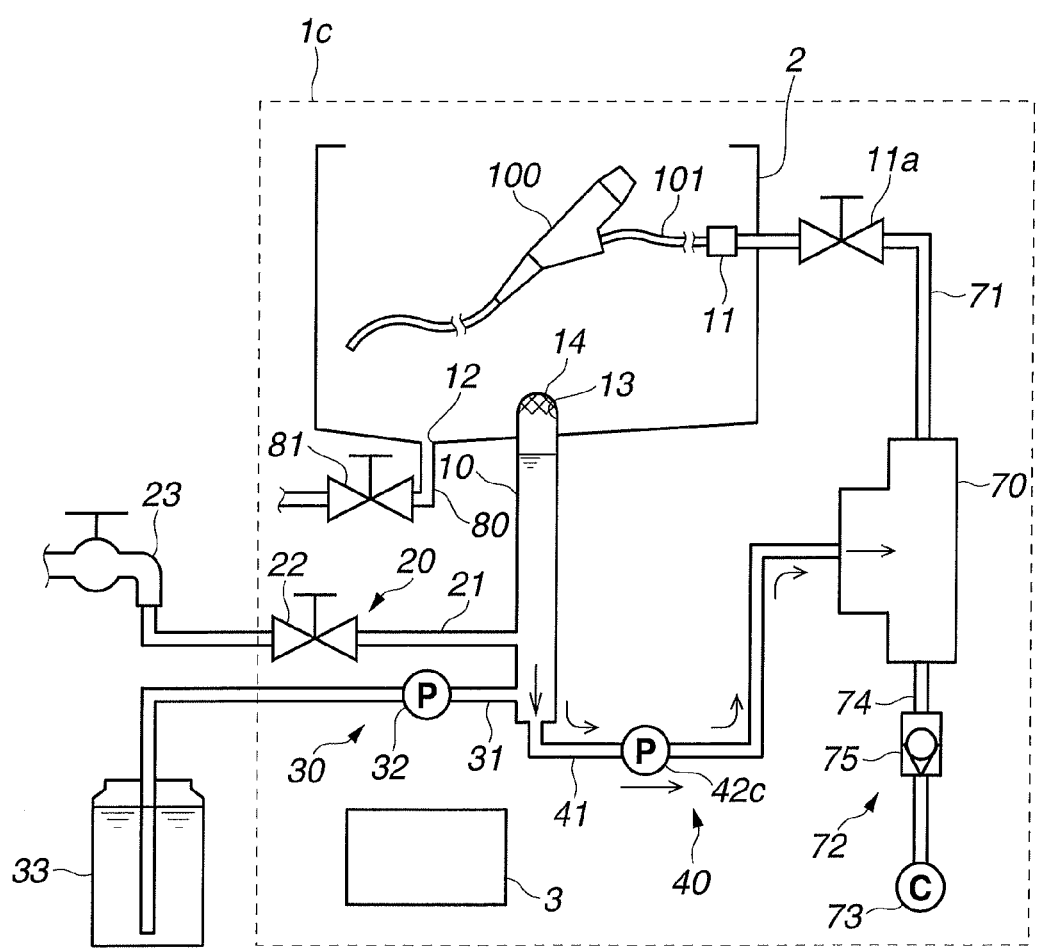
FIG. 11 is a view illustrating a configuration of an endoscope apparatus according to a third embodiment.

As shown in FIG. 11, an endoscope processing apparatus 1c according to the present embodiment is configured such that the multipurpose conduit 10 and the gas-liquid mixing section 70 are connected only by the liquid-feeding section 40. In addition, the liquid-feeding section 40 according to the present embodiment is configured by the liquid-feeding conduit 41 and an electric pump 42c which is operable forward and reversely and which can bi-directionally transfer the fluid in the liquid-feeding conduit 41. Note that it is preferable that the electric pump 42c is configured to be able to change the flow rate.

That is, the endoscope processing apparatus 1c according to the present embodiment is not provided with the stirring conduit 60 and the opening/closing section 61 which are provided in the endoscope processing apparatus 1 in the first embodiment. Furthermore, in the endoscope processing apparatus 1 in the first embodiment, the liquid-feeding section 40 is configured by the two conduits and the two electric pumps. However, the liquid-feeding section 40 according to the present embodiment is configured by one liquid-feeding conduit 41 and one electric pump 42c.

Figure 12:
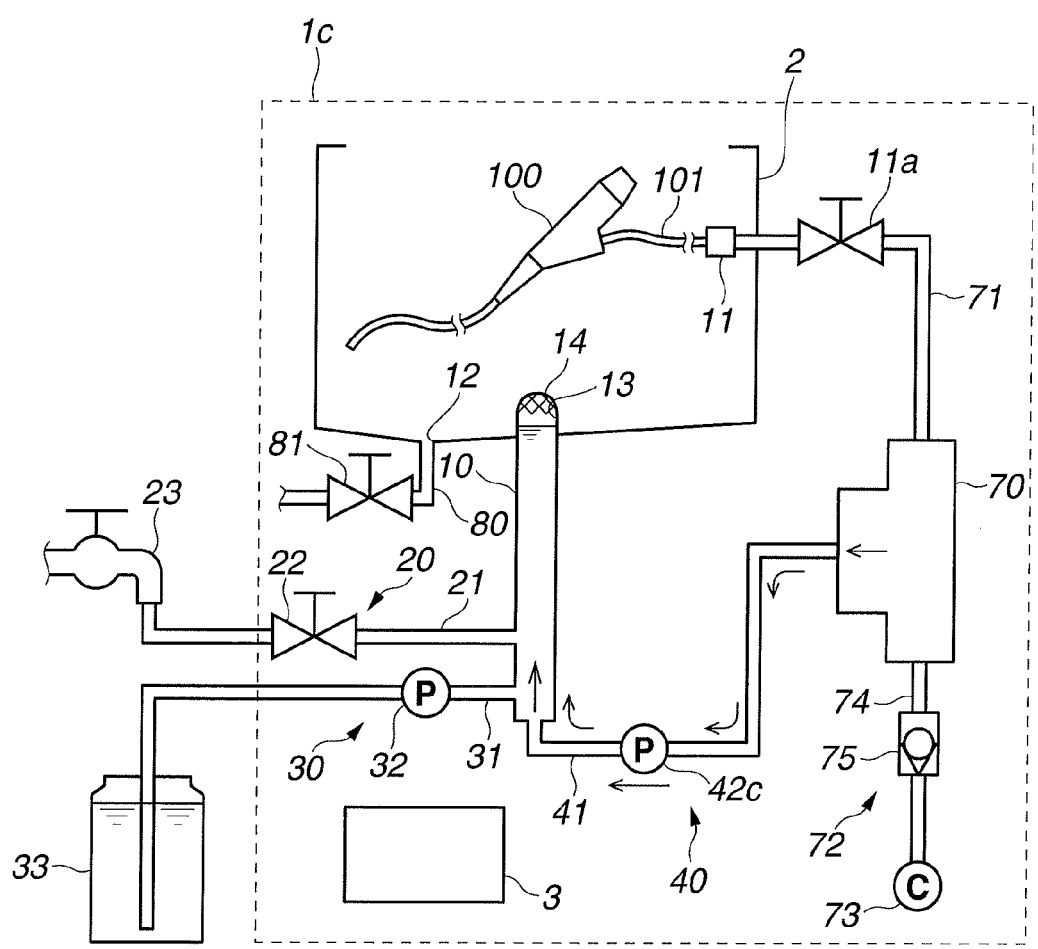
FIG. 12 is a view illustrating a stirring process in the third embodiment.

In the endoscope processing apparatus 1c according to the present embodiment as described above, in the stirring process in the step S04, the electric pump 42c is operated so as to alternately repeat the operation for transferring the fluid in the liquid-feeding conduit 41 from the multipurpose conduit 10 toward the gas-liquid mixing section 70 as shown in FIG. 11 and the operation for transferring the fluid in the liquid-feeding conduit 41 from the gas-liquid mixing section 70 toward the multipurpose conduit 10 as shown in FIG. 12. That is, the forward direction operation and reverse direction operation of the electric pump 42c are alternately repeated.

In the step S04, the forward direction operation and the reverse direction operation of the electric pump 42c are alternately repeated, thereby causing the mixed liquid in the multipurpose conduit 10 to move back and forth between the multipurpose conduit 10 and the gas-liquid mixing section 70 through the liquid-feeding conduit 41.

As described above, also with the configuration of the endoscope processing apparatus 1c according to the present embodiment, it is possible to perform the stirring process for stirring the mixed liquid of the tap water and the medicinal solution stored in the multipurpose conduit 10. The endoscope processing apparatus 1c according to the present embodiment can be configured in a reduced size with a simpler configuration, because there is no need for providing the stirring conduit 60, the opening/closing section 61, and the one conduit and the electric pump constituting the liquid-feeding section 40 which are provided in the endoscope processing apparatus 1 in the first embodiment.

Note that the present invention is not limited to the above-described embodiments, and appropriate modifications are possible without departing from the gist or spirit of the invention which can be read from claims and throughout the description, and also an endoscope processing apparatus and an endoscope processing method involving such modifications are also included in the technical range of the present invention.

As described above, the present invention is preferable for an endoscope processing apparatus that processes an endoscope with two-phase gas-liquid flow using a mixed liquid obtained by mixing a plurality of liquids.

What is claimed is:

1. An endoscope processing apparatus comprising:
a cleaning tank configured to be able to house at least one of an endoscope and endoscope accessories;
a liquid drainage port which is an opening portion provided to a bottom surface of the cleaning tank;
a liquid inlet port which is an opening portion provided to open at an upper position than the liquid drainage port in the cleaning tank;
a discharge port which is an opening portion provided to the cleaning tank;
a multipurpose conduit including the liquid inlet port and having a predetermined capacity;
a first-liquid introducing section directly connected to the multipurpose conduit and configured to introduce a first liquid into the multipurpose conduit;
a second-liquid introducing section directly connected to the multipurpose conduit and configured to introduce a second liquid into the multipurpose conduit;
a gas-liquid mixing section connected to the multipurpose conduit and the discharge port, and configured to mix a liquid in the multipurpose conduit and gas, to deliver the mixed fluid to the discharge port;
a discharge valve disposed between the discharge port and the gas-liquid mixing section, and configured to open and close a connection between the discharge port and the gas-liquid mixing section;
a liquid-feeding section including a liquid-feeding conduit and a liquid-feeding pump, the liquid-feeding conduit having one end connected to the multipurpose conduit and another end connected to the gas-liquid mixing section, the liquid-feeding pump being provided to the liquid-feeding conduit and configured to deliver a liquid in the multipurpose conduit to the gas-liquid mixing section;
a stirring conduit having one end connected to the multipurpose conduit and another end connected to the gas-liquid mixing section;
an opening/closing section provided to the stirring conduit, and configured to open and close a connection between the multipurpose conduit and the gas-liquid mixing section; and
a compressor connected to the gas-liquid mixing section, and configured to deliver the gas to the gas-liquid mixing section,
wherein, when the discharge valve is closed, the opening/closing section is opened, and the liquid-feeding pump is driven, a route is configured in which a liquid in the multipurpose conduit circulates by passing through only the multipurpose conduit, the liquid-feeding conduit, the gas-liquid mixing section, and the stirring conduit.

2. The endoscope processing apparatus according to claim 1, wherein the multipurpose conduit is configured such that an uppermost portion thereof is connected to the liquid inlet port.

* * * * *